United States Patent [19]

Morgan

[11] Patent Number: 4,605,736

[45] Date of Patent: Aug. 12, 1986

[54] TITANIUM-GLYCOL USEFUL, AS CROSSLINKING AGENTS, FOR POLYGALACTOMANNANS

[75] Inventor: Michael E. Morgan, Louisville, Ky.

[73] Assignee: Celanese Corporation, New York, N.Y.

[21] Appl. No.: 743,246

[22] Filed: Jun. 11, 1985

[51] Int. Cl.$^4$ .............................................. C07H 1/00
[52] U.S. Cl. ................................... 536/114; 536/121; 536/124
[58] Field of Search ..................... 536/114, 121, 124

[56] References Cited

U.S. PATENT DOCUMENTS

| | | | |
|---|---|---|---|
| 3,301,723 | 1/1967 | Chrisp | 149/20 |
| 3,697,498 | 10/1972 | Browning et al. | 536/114 |
| 4,033,415 | 7/1977 | Holtmyer et al. | 166/308 |
| 4,043,952 | 8/1977 | Ganslaw et al. | 536/114 |
| 4,324,668 | 4/1982 | Harris | 252/8.55 C |
| 4,488,975 | 12/1984 | Almond | 252/8.55 R |
| 4,502,967 | 3/1985 | Conway | 252/8.55 R |

*Primary Examiner*—Johnnie R. Brown
*Attorney, Agent, or Firm*—Herbert P. Price

[57] ABSTRACT

Aqueous solutions of polygalactomannans are crosslinked with the reaction product of titanium tetrachloride and a water-soluble alcohol or diol. Such crosslinked products are useful in fracturing solutions for secondary oil recovery or in gel explosives.

13 Claims, No Drawings

TITANIUM-GLYCOL USEFUL, AS CROSSLINKING AGENTS, FOR POLYGALACTOMANNANS

BACKGROUND OF THE INVENTION

The field of art to which this invention pertains is the process of crosslinking polygalactomannans.

Use of thickening agents and gelling agents for the purpose of increasing viscosity of water or water solutions has been known for many years. Among most widely used thickeners are those compounds generally characterized as hydroxylated polymers which contain vicinal bis-hydroxyl groups. The most readily available of these polymers are the polygalactomannans and their derivatives. These polymer gums form viscous solutions in water which function is accomplished by absorption of large amounts of water by the polymer or by dissolution of the polymer gum in water or both. The degree of thickening and the viscosity of the water to which the polymer is added will depend upon the quantity and kind of polymer used. A wide range of solution properties can be produced by the selection of particular gums and by the adjustment of the quantities used and the temperature of the reaction medium. These polymer gums have found wide application in the textile, food, pharmaceutical, explosive, mining and oil field industries.

A useful property of the polygalactomannan gums is their ability to form firm gels when crosslinked by various agents. Well-known crosslinking agents are borates, pyroantimonates and chelates of the transition metals, e.g., titanium. Heretofore, the use of titanium compounds has been limited to highly acidic media or to pH's of 6 or higher.

In U.S. Pat. No. 4,033,415, it is stated that titanium tetrachloride will not cause crosslinking of a gelling agent at a pH of more than 2; however, when added to a medium containing an aqueous liquid and a gelling agent, the titanium tetrachloride reacts to form the intermediate hydroxide in hydrochloric acid in sufficient quantities to adjust the pH of the medium to less than 2 where crosslinking will occur. Another disadvantage of using titanium tetrachloride is that it reacts violently when added to aqueous media.

In U.S. Pat. No. 3,301,723, it is stated that bases must be used with transition metal compounds in order to obtain practical crosslinking reactions. Without base, compounds of only a few of the transition metals, namely, vanadium, titanium and zirconium compounds, will cause crosslinking to occur. However, compounds of these metals alone do not produce extensive gelation unless they are used in high concentrations, i.e., usually at least in an order of magnitude greater than the concentrations that are effective for crosslinking when base is present. In addition to being less economically attractive, such concentrations of crosslinking agents can cause degradation of the gel structure or other undesirable side reactions. Furthermore, unless base is present, wide variations in the extent and rate of crosslinking may occur so that reproducible control of the process becomes very difficult.

In U.S. Pat. No. 4,324,668, the statement is made that crosslinking agents containing metals, such as aluminum, chromium, titanium, boron, lead, zinc, tin and antimony, do not function satisfactorily in aqueous highly acidic media.

The present invention provides a process for crosslinking polygalactomannans with titanium compounds in aqueous systems wherein the crosslinked system has a pH of about 2.5 to about 6.

SUMMARY OF THE INVENTION

In one aspect, this invention pertains to a process for crosslinking polygalactomannans. In another aspect, this invention relates to a process for crosslinking polygalactomannans using titanium-alcohol or diol complexes.

The compositions useful in this invention are made by dissolving titanium tetrachloride in a water-soluble organic alcohol or diol at a concentration of about 1 to about 50 weight percent, preferably about 1 to about 35 weight percent, based on the weight of the titanium tetrachloride and alcohol or diol solution, followed by reaction with 0 to about 3 equivalents of base per mole of titanium tetrachloride and then by filtration to remove the salt formed in the reaction when base is used.

When the titanium complexes of this invention are mixed with aqueous polygalactomannan solutions having a pH of about 4 to about 8, the pH after the titanium addition drops to about 2.5 to about 6 and firm crosslinked gels are obtained.

DESCRIPTION OF THE INVENTION

The transition metal useful in this invention is titanium in the form of titanium tetrachloride.

The organic alcohols and diols useful in this invention are water-soluble and contain primary or secondary hydroxyl groups. Useful alcohols are those which contain 1 to 3 carbon atoms, such as methanol, ethanol or isopropanol. Useful diols are those which contain 2 to 8 carbon atoms, such as ehtylene glycol, 1,2-propylene glycol, 1,3-propylene glycol, 1,4-butylene glycol, 1-4-pentanediol, 1,7-heptanediol and the like. Also included among the alcohols and diols useful in this invention are the water-soluble polyoxy-alkylene glycols and water soluble monoalkyl ethers of glycols and polyoxyalkylene glycols. Examples of such polyoxyalkylene glycols are polyoxyethylene glycols and polyoxypropylene glycols having molecular weights up to about 600. Examples of monoalkyl ethers of glycols include monomethyl ether of ethylene glycol, monoethyl ether of ethylene glycol, monobutyl ether of ethylene glycol, monomethyl ether of propylene glycol, monobutyl ether of propylene glycol, monomethyl ether of diethylene glycol, monoethyl ether of diethylene glycol, monobutyl ether of diethylene glycol and the like. The preferred alcohol or diol for use in this invention is ethylene glycol.

Bases useful in this invention are alkali metal hydroxides, alkaline earth metal hydroxides and alkali metal bicarbonates and carbonates. Examples of such bases include lithium hydroxide, sodium hydroxide, potassium hydroxide, sodium bicarbonate, sodium carbonate, potassium carbonate and calcium hydroxide. The preferred base is sodium hydroxide which, preferably, is added as an aqueous solution containing 30 to about 50 weight percent sodium hydroxide.

Polygalactomannans useful in this invention are guar, locust bean gum and various derivatives. Examples of such derivatives include hydroxyethyl guar, hydroxypropyl guar, carboxymethyl guar, carboxyethyl guar, hydroxyethyl carboxymethyl guar, hydroxypropyl carboxymethyl guar and quaternary derivatives such as those made by reacting guar or locust bean gum with 1-chloro-2-hydroxypropyl trimethylammonium chloride. The preferred polygalactomannans are underivatized guar and hydroxypropyl guar.

In preparing the compositions of this invention, titanium tetrachloride is added to the alcohol or diol to form a solution containing about 1 to about 50 weight percent, preferably, about 1 to about 35 weight percent titanium tetrachloride based on the weight of titanium tetrachloride and alcohol or diol. Such solutions of the titanium tetrachloride and alcohol or diol are useful as crosslinking agents with no further treatment; however, the preferred compositions are those which have been reacted further with a base in the amount of about 1 equivalent to about 3 equivalents of base per mole of titanium tetrachloride in the alcohol or diol. Most preferred are compositions which have been reacted with 1 to 2 equivalents of base. When bases are used, the solutions are filtered to remove the salt formed in the reaction.

In preparing the crosslinking agents useful in this invention, the titanium tetrachloride is added to the alcohol or diol at such a rate that the temperature due to the exothermic reaction does not exceed about 70° C. Generally, this addition rate will vary from about 10 minutes to about 4 hours depending on the batch size, excess alcohol or diol and characteristics of the reactor. The temperature during the titanium tetrachloride addition will vary between ambient temperatures (15°–25° C.) to about 70° C. Base is added to the titanium tetrachloride alcohol, diol reactants at such a rate that the exothermic acid-base reaction does not exceed about 90° C. Generally this addition time will be about 10 minutes to about 2 hours. The temperature during the addition vary from ambient temperatures (15°–25° C.) to about 90° C., preferably, about 45° to about 60° C.

The process of this invention, i.e., the crosslinking of polygalactomannans, is conducted using aqueous solutions of the polygalactomannans. Useful solutions contain about 20 to about 120 pounds of the polyglactomannan per 1000 gallons of water and, preferably, about 30 to about 50 pounds per 1000 gallons of water. For use in this invention, the polygalactomannan solutions will have a pH of about 4 to about 8. The titanium tetrachloride-alcohol or diol crosslinking agent is added to the polyglacto-mannan solution in the amount of about 0.005 millimoles to about 5 millimoles of titanium per gram of the polygalactomannan and, preferably, about 0.2 to about 0.5. The pH of the crosslinked system will be about 2.5 to about 6.

The crosslinked compositions made by the process of this invention are useful in fracturing fluids used in secondary recovery process of the oil well industry. Such compositions are also useful in the manufacture of gelled explosives.

The invention is explained in more detail by the following examples. Parts and percentages unless otherwise indicated are parts and percentages by weight.

EXAMPLE 1

To a suitable reactor containing 425 parts of ethylene glycol were added 75 parts of titanium tetrachloride (0.39 mole) with stirring over a 1 hour period with the temperature rising from 26° C. to 45° C. When all the titanium tetrachloride had dissolved, the temperature was lowered to 40° C. and 21 parts of sodium carbonate were added over a 10 minute period with the temperature rising to 45° C. When the addition was completed, the mixture was heated to 60° C. for one hour. The reactants were then cooled to room temperature and were filtered to remove the sodium chloride formed in the reaction.

EXAMPLE 2

To a suitable reactor containing 450 parts of ethylene glycol were added with stirring 50 parts of titanium tetrachloride (0.26 mole) over a one hour period with the temperature rising from 24° C. to 43° C. When all the titanium tetrachloride had dissolved, and with the temperature at 39° C., 32.4 parts of a 45% aqueous potassium hydroxide solution were added over a half hour period with the temperature rising to 44° C. The reactants were then heated to 60° C. and were held at 60° C. for one hour. The reactants then cooled to room temperature and were filtered to remove the potassium chloride formed in the reaction.

EXAMPLE 3

Using the same procedure as described in the preceding examples, 25 parts of titanium tetrachloride (0.130 mole) were reacted in 475 parts of ethylene glycol followed by reaction with 14 parts of sodium carbonate.

EXAMPLE 4

Using the same procedure as described in the preceding examples, 175 parts of titanium tetrachloride (0.919 mole) were reacted in 325 parts of ethylene glycol followed by reaction with 73.5 parts of a 50% aqueous sodium hydroxide solution.

EXAMPLE 5

Using the same procedure as described in the preceding examples, 100 parts of titanium tetrachloride (0.52 mole) were reacted in 400 parts of ethylene glycol followed by reaction with 124 parts of a 50% aqueous sodium hydroxide solution.

EXAMPLE 6

The crosslinking agents prepared in the preceding examples were evaluated as follows: A hydroxypropyl guar solution was prepared at a concentration of 40 pounds per 1000 gallons by dissolving the hydroxypropyl guar in water containing 2% potassium chloride. The pH of the solution was adjusted to 4.2 with acetic acid. 700 mls of the gum solution, which had a viscosity of 30 to 35 cps, were measured into a closed loop connected to a gear pump. The gum solution was circulated through the loop at the maximum speed of the gear pump (1700 rpm). The amount of crosslinker indicated in the table was injected into the system and allowed to circulate for 1 minute. 65 mls of the resulting gel were loaded into a viscometer cup and placed on the Fann 50 viscometer. The viscosity was determined at 130° F. (preheated bath) at 300 rpm. The viscosity results were as follows:

| Cross-linking Agent | Amount Gal./1000 Gal. | Temp. °F. | Viscosity (cps) | | |
|---|---|---|---|---|---|
| | | | Init. | 30 Min. | 60 Min. |
| Example 1 | 2.6 | 130 | 500 | 669 | 606 |
| Example 2 | 1.3 | 130 | 152 | 106 | 106 |
| Example 3 | 2.6 | 130 | 152 | 98 | — |
| Example 4 | 0.7 | 130 | 535 | 624 | 562 |
| Example 5 | 2.6 | 130 | 268 | 428 | 580 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed:

1. A process for crosslinking polygalactamannans which comprises adding to an aqueous solution of polygalactomannans having a pH of about 4 to about 8 a crosslinking agent which is titanium tetrachloride dissolved in a water-soluble organic alcohol or diol at a concentration of about 1 to about 50 weight percent based on the total weight of titanium tetrachloride and water-soluble organic alcohol or diol, and wherein the pH after the addition is about 2.5 to about 6.

2. The process of claim 1 wherein the titanium tetrachloride is dissolved in the water-soluble organic alcohol or diol at a concentration of about 1 to about 35 weight percent.

3. The process of claim 1 wherein the solution of titanium tetrachloride and water-soluble organic alcohol or diol is reacted with 0 to about 3 equivalents of base for each mole of titanium tetrachloride.

4. The process of claim 3 wherein the base is an aqueous solution of sodium hydroxide.

5. The process of claim 1 wherein the diol is ethylene glycol.

6. The process of claim 1 wherein the aqueous solution of polygalactomannan contains about 20 to about 120 pounds of polygalactomannan per 1000 gallons of water.

7. The process of claim 1 wherein the aqueous solution of polygalactomannan contains about 30 to about 50 pounds of polygalactomannan per 1000 gallons of water.

8. The process of claim 1 wherein the titanium tetrachloride crosslinking agent is added to the aqueous solution of polygalactomannan in the amount of about 0.005 millimole to about 5 millimole of titanium per gram of the polygalactomannan.

9. The process of claim 1 wherein the titanium tetrachloride crosslinking agent is added to the aqueous solution of polygalactomannan in the amount of about 0.2 to about 0.5 millimole of titanium per gram of the polygalactomannan.

10. The process of claim 1 wherein the polygalactomannan is guar gum.

11. The process of claim 1 wherein the polygalactomannan is hydroxypropyl guar.

12. A process for crosslinking polygalactomannans selected from the group consisting of underivatized guar and hydroxypropyl guar which comprises adding to an aqueous solution of the polygalactomannan having a concentration of about 20 pounds to about 120 pounds of polygalactomannan per 1000 gallons of water, said solution having a pH of about 4 to about 8, a crosslinking agent which is titanium tetrachloride dissolved in ethylene glycol at a concentration of about 1 to about 50 weight percent based on the total weight of titanium tetrachloride and glycol, wherein the crosslinking agent is added in the amount of about 0.005 millimole to about 5 millimoles of titanium per gram of polygalactomannan and wherein the pH after the addition is about 2.5 to about 6.

13. The process of claim 12 wherein the aqueous solution of polygalactomannan contains about 30 to about 50 pounds of polygalactomannan per 1000 gallons of water, and wherein the concentration of titanium tetrachloride in glycol is about 1 to about 35 weight percent based on the weight of titanium tetrachloride and glycol.

* * * * *